United States Patent
Guerra et al.

(10) Patent No.: US 10,055,929 B2
(45) Date of Patent: Aug. 21, 2018

(54) AUTOMATED EYEWEAR KIOSK

(71) Applicant: ESSILOR INTERNATIONAL, Charenton-le-Pont (FR)

(72) Inventors: John Guerra, Dallas, TX (US); Pamela Anne McClimans, Dallas, TX (US); Peiqi Jiang, Dallas, TX (US); Susie Wood, Dallas, TX (US); Mark Hale, Dallas, TX (US); Christina Urbanski, Dallas, TX (US); Roy Karr, Dallas, TX (US)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/540,976

(22) PCT Filed: Dec. 31, 2014

(86) PCT No.: PCT/IB2014/003145
§ 371 (c)(1),
(2) Date: Jun. 29, 2017

(87) PCT Pub. No.: WO2016/108065
PCT Pub. Date: Jul. 7, 2016

(65) Prior Publication Data
US 2018/0012440 A1  Jan. 11, 2018

(51) Int. Cl.
*G07F 17/02* (2006.01)
*G06F 19/00* (2018.01)
(Continued)

(52) U.S. Cl.
CPC .......... *G07F 17/02* (2013.01); *G06F 19/3418* (2013.01); *G06Q 30/0635* (2013.01); *G07F 11/70* (2013.01)

(58) Field of Classification Search
CPC ....... G07F 11/70; G07F 17/02; G06F 19/3418
(Continued)

(56) References Cited

U.S. PATENT DOCUMENTS 6,682,195 B2 *  1/2004  Dreher ................. G02C 13/003
                                                            351/204
6,792,401 B1     9/2004  Nigro et al.
(Continued)

FOREIGN PATENT DOCUMENTS

WO    2010077919 A1    7/2010

OTHER PUBLICATIONS

ISR/WO for International Appln. No. PCT/IB2014/003145; dated Aug. 20, 2015.

Primary Examiner — Michael Collins
(74) Attorney, Agent, or Firm — Oblon, McClelland, Maier & Neustadt, L.L.P.

(57) ABSTRACT

A self-service kiosk for dispensing eyewear is disclosed. The kiosk includes a display for depicting available frame and lens options to customers. A user interface accepts eyewear order information from a customer including the customer's prescription information and frame selection. The kiosk also includes a lens manufacturing device that is wholly contained within the kiosk for manufacturing optical lenses in the prescription of the customer, which are adapted for the selected frame. Further, the kiosk includes a dispensing mechanism for dispensing from the kiosk the manufactured lenses, along with the customer selected frame.

13 Claims, 3 Drawing Sheets

(51) Int. Cl.
*G06Q 30/06* (2012.01)
*G07F 11/70* (2006.01)

(58) Field of Classification Search
USPC .................................................. 700/231–244
See application file for complete search history.

(56) References Cited

U.S. PATENT DOCUMENTS

| | | | |
|---|---|---|---|
| 7,384,146 B2* | 6/2008 | Covannon | A61F 9/008 351/206 |
| 8,740,386 B2* | 6/2014 | Foster | A61B 3/18 351/246 |
| 9,330,408 B2* | 5/2016 | Werzer | G06Q 30/0621 |
| 2006/0290885 A1* | 12/2006 | Covannon | A61F 9/008 351/212 |
| 2008/0288369 A1 | 11/2008 | Hunter | |
| 2014/0257839 A1 | 9/2014 | Suter et al. | |
| 2015/0088307 A1* | 3/2015 | Ackerman | G06Q 10/087 700/241 |

* cited by examiner

AUTOMATED EYEWEAR KIOSK

FIELD OF THE INVENTION

Embodiments of the invention are directed, in general, to providing a self-serve vending solution for eyewear, such as spectacle lenses, eyeglass frames, sunglasses, and reading glasses.

BACKGROUND OF THE INVENTION

Traditionally, customers seeking to obtain new eyeglasses are limited to making purchases at retail outlets. Such purchases usually require the assistance of an optician or a sales associate. Typically, the customer first obtains a prescription from an ophthalmologist and then visits an optician to choose a frame style for the eyeglasses. The customer may try several frames before selecting a desired frame. The optician then orders a pair of lenses corresponding to the prescription and adapted for the selected frames. Retail eyeglasses sales require trained opticians to take optical measurements, input the prescription, and order lenses from a laboratory. More recent advances in online selling of eyeglasses also do not address the needs of customers in rural locations, which often have little to no industrialization or lack adequate eyeglass resources. Existing solutions do not adequately address the time-consuming nature of multiple trips often being necessary when making a traditional retail purchase, nor minimize the wait time for glasses ordered online to be received.

The current processes for purchasing eyeglasses limit the customer's choice as to location (i.e., at an optician's location) and timing (i.e., during the hours of the optician's retail operation and/or after a wait of days or weeks for lenses to return from being manufactured in a lab). Additionally, in the current ordering process, customers may be subject to a high-pressure sales environment at the optician's retail outlet. These factors can lengthen the purchase cycle for prescription eyewear and may deter customers seeking to change frame styles or purchase extra eyeglasses. Consumers would benefit from a process that makes it easier and more economical to purchase eyewear without having to wait for the eyewear to be delivered from a remote location or return to an optician's location to receive the eyewear.

SUMMARY OF THE INVENTION

The present invention is directed to an automated eyewear kiosk and methods for dispensing eyewear. In one implementation, the kiosk comprises a display configured to depict available frame and lens options to a customer and a user interface configured to receive eyewear order information. The order information comprises customer prescription information and frame selection. The kiosk additionally comprises a lens manufacturing device being wholly contained within the kiosk and configured to manufacture lenses, in the prescription of the customer, adapted for the selected frame. A dispensing mechanism configured to dispense the manufactured lenses and selected frame from the kiosk is also included.

In another implementation, an automated eyewear kiosk is described. The kiosk comprises a display configured to depict available frame options and lens options to a customer and a user interface configured to receive eyewear order information. The eyewear order information comprises an optical lens prescription, lens options, and frame selection. The kiosk additionally comprises a dispensing mechanism configured to dispense pre-made lenses corresponding to the eyewear order information. The pre-made lenses comprise tab connectors integrated into the lens for securing the lens to the selected frame. The selected frame may also comprise an adjustable bridge.

Another implantation for dispensing eyewear comprises receiving order data at a kiosk, where the order data comprises optical lens prescription information, a frame selection, and patient identification data. The implementation additionally includes dispensing, from the kiosk, optical lenses corresponding to the received optical lens prescription information and where the optical lenses are manufactured with tabs to secure the lenses to the selected frame. The implementation additionally includes dispensing, from the kiosk, the selected frames, where the frames are manufactured with corresponding sockets to secure the optical lenses. In one implementation, the frame selection received includes a request for more than one frame in which the lenses may be secured. In other implementations, receiving order data also includes receiving a request for more than one type of lens, with each lens being compatible with the frame(s) selected.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Figure 1:
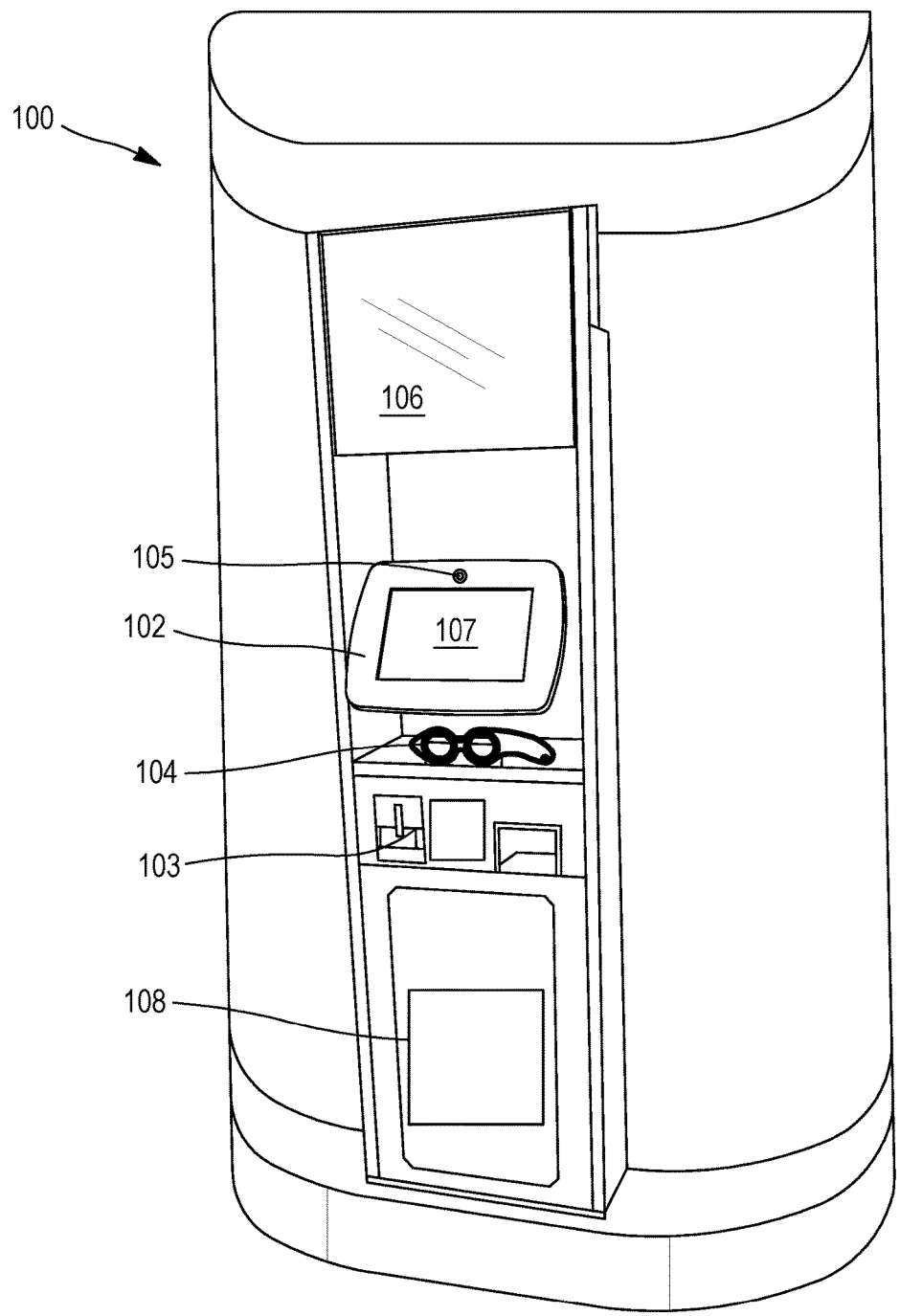
Figure 2:
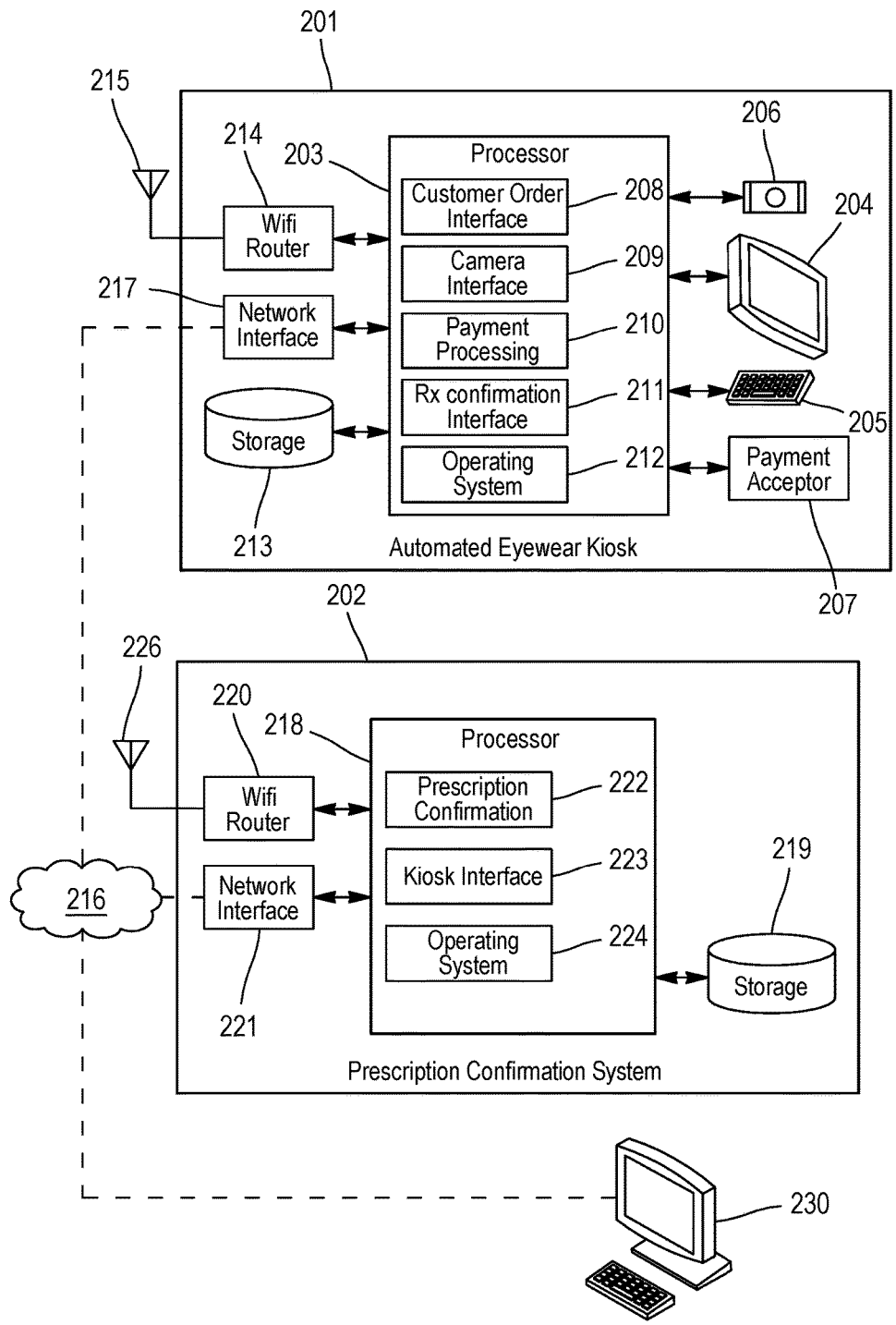
Figure 3:
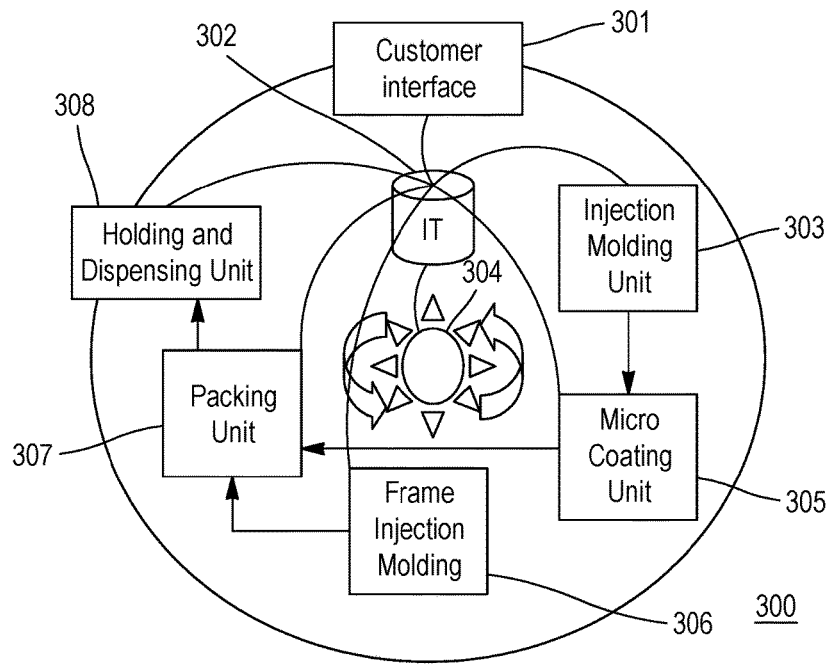
Figure 4:
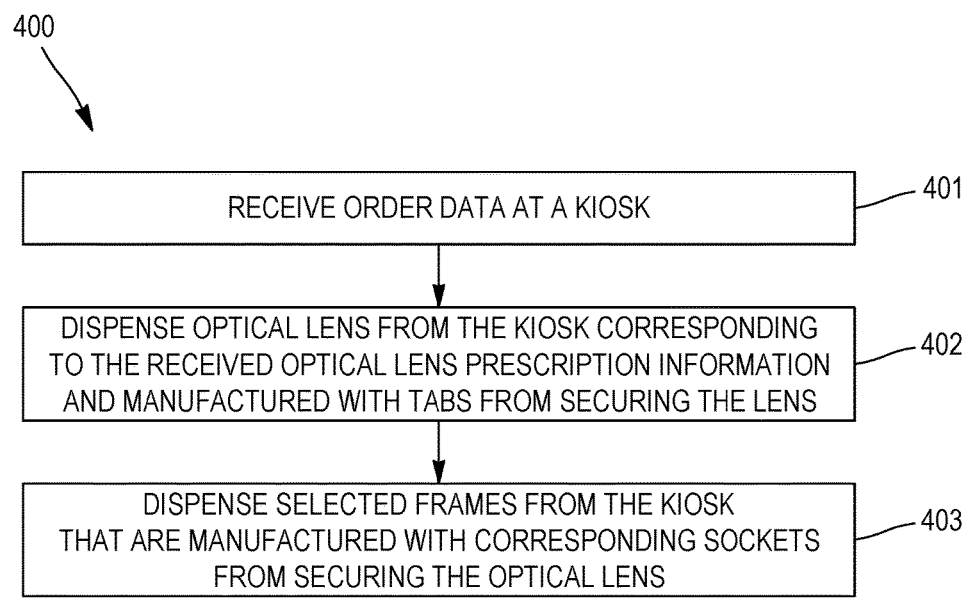

Having thus described the invention in general terms, reference will now be made to the accompanying drawings, wherein:

FIG. 1 illustrates an automated eyewear kiosk according to one embodiment;

FIG. 2 is a block diagram of various components of an automated eyewear kiosk;

FIG. 3 is a block diagram of various components of an embodiment of an automated eyewear kiosk; and FIG. 4 is a flowchart illustrating a process for fulfilling customer orders for eyewear according to one embodiment.

DETAILED DESCRIPTION OF THE INVENTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

Example embodiments of an automated eyewear kiosk are disclosed. Customers seeking to purchase eyewear, whether conforming to an optical prescription or not, may use the kiosk instead of having to shop in traditional retail environments. Customers may use the kiosk to obtain eyewear for a new prescription, to obtain secondary pairs of glasses for existing prescriptions, obtain glasses with no prescription, but with another characteristic, such as sun wear or sport glasses, and/or any number of other possibilities. In various embodiments, customers may try on various frames styles and then directly order the eyewear, including the selected frame, using the kiosk. In other embodiments, a representation of the available frames may be provided using a picture, or may be presented virtually on a display screen of the kiosk, rather than being physically on display. In various disclosed embodiments, the kiosk comprises all components needed for self-contained manufacturing of a pair of glasses, which is triggered by a customer or other individual inputting an order into the kiosk. In addition to the kiosk allowing customers to evaluate available lens options or upgrades, as well as multiple frame styles in a no-pressure sales environment, the customer is able to receive the glasses in a much shorter period of time, without having to wait days to receive purchased eyewear.

FIG. 1 illustrates an automated eyewear kiosk 100 according to one embodiment. Kiosk 100 comprises, for example, a user interface 102, payment interface 103, lorgnette 104, camera 105, and mirror 106. In various embodiments, additional components may be present, and some components shown will not be used. Kiosk 100 is merely illustrative of one possible embodiment.

In various disclosed embodiments, the user interface 102 includes a touch screen 107. The touch screen 107 allows a user, such as an eyewear customer, to interact with the kiosk 100 for eyewear selection and ordering purposes. The touch screen 107 may display one or more images of frames that are available from the kiosk 100 for customer selection. In other embodiments, in addition to, or instead of displaying frame images on the touch screen 107, sample frames (not shown) may be provided for demonstration and style-selection purposes. The frames may have a tag or other label, sticker, or other marking that indicates a unique frame code for a particular frame style, which can be used as input when ordering from the user interface 102. When sample frames are physically available from the kiosk 100, customers may use mirror 106 when trying on and selecting a frame style.

Once the customer has selected a desired frame style, either from the image presented on the touch screen 107 or the sample frames provided, he or she will then be presented with lens options that are available for the frame. Available lens options may include material indexes (such as orma, poly, hi index), lens type (such as single vision, progressive, solar, etc.), and added value treatments (such as polarized, anti-reflective coatings, photochromic coatings, tints, hard material coatings, etc.), as well as other options not specifically described.

In one or more embodiment, lorgnette 104 and camera 105 may be used to measure the customer's pupillary distance. The camera 105 may also be used to capture one or more images, a video clip, or provide live video of the customer for use in a virtual try on application that can be initiated from the user interface 102 and displayed on the touch screen 107.

The kiosk 100 additionally comprises payment interface 103, to facilitate payment for the eyewear. In various embodiments, the kiosk 100 further includes a holding and dispensing unit 108 for holding eyewear that is ready to be dispensed to customers, as well as dispensing the eyewear when appropriate.

FIG. 2 is a block diagram of various components of an automated eyewear kiosk 201, which in various embodiments, is in communication with a prescription confirmation system 202. Kiosk 201 comprises a processor 203, user interface display 204, user interface keypad 205, camera 206, and payment acceptor 207. Processor 203 controls and coordinates the operation of kiosk 201 and its components using one or more software applications 208-212. Storage device 213 may be used to store software code and instructions for applications 208-212 and other data, such as customer account information and order information. Storage device 213 may be any appropriate memory device or computer storage media, such as, but not limited to, a hard disk drive, RAM, ROM, EEPROM, flash memory or other memory technology, CD-ROM, digital versatile disks (DVD) or other optical disk storage, magnetic cassettes, magnetic tape, magnetic disk storage or other magnetic storage devices. Kiosk 201 may be in communication with a prescription ordering system 202 via a wireless or wired network connection. In various embodiments, a WiFi router 214 or other wireless transceiver supports wireless communications with the prescription confirmation system 202 either directly or through one or more intermediate access points or networks (not shown) using radio frequency (RF) signals transmitted and receive using antenna 215. The WiFi router 214 may also be used to allow customers to remotely connect to the kiosk 201 directly for ordering eyewear, to be dispensed from and/or manufactured within the kiosk 201.

In other embodiments, kiosk 201 communicates with the prescription confirmation system 202, or remote customer, via a public or private network(s) 216, such as the Internet, an intranet, or any other packet data network, which is accessed via a network interface 217.

Customer order interface application 208 provides outputs to display 204, such as instructions and other information for the customer. Customer order interface application 208 also receives input from the customer, such as via a touch-sensitive screen on display 204 or via keypad 205. In other embodiments, the customer may interact with kiosk 201 in any appropriate manner, such as using speech inputs, thumb scan, eye scan, and audio outputs, or any other similar input or output means. The user may input an optical prescription, selected frame style, lens type and options, account or personal information, and any other appropriate or required information in response to visual or audio prompts generated by customer order interface 208.

The customer order interface application 208 may additionally trigger the kiosk 201 to begin the manufacturing of the selected frames and/or lenses, when applicable, by sending instructions to various manufacturing components related to the frames and/or lenses that are being manufactured within the kiosk 201. Manufacturing components are described in greater detail in FIG. 3 below. In various embodiments, customer order interface application 208 additionally communicates instructions to holding and dispensing components (also described below in FIG. 3) related to frames and/or lenses that are manufactured remotely and dispensed from the kiosk 201.

In various embodiments, a camera interface application 209 is used to calculate the customer's pupillary distance for use in manufacturing the selected eyewear, when appropriate. Additionally, the camera interface application 209 is used in various embodiments to deliver a "virtual try on"

experience for customers, allowing the customer to visualize how eyewear will look on him or her. Allowing for virtual try on is particularly useful when there are no physical samples available as part of the kiosk 201.

Payment processing application 210 is used to accept and process payment information for a customer. Payment processing application 210 may work with payment acceptor 207, which may accept credit/debit cards (e.g., magnetic card swipe), cash, tokens, coupons, gift cards, NFC or other mobile payment, or any other form of payment.

In various embodiments, prescription confirmation application 211 coordinates communication with prescription confirmation system 202, when appropriate and/or allowed, for verifying that a prescription is valid and is accurate. Prescription confirmation application 211 exchanges customer identification information and eyewear prescription information with prescription confirmation system 202.

Operating system 212 manages resources for processor 203 and provides services for applications 208-211 and other programs Applications 208-211 may be components of operating system 212 or may be separate software programs running on processor 203.

In one embodiment, some components of automated eyewear kiosk 201 may correspond to a portable computing device, such as a tablet computer, smartphone, PDA, laptop computer, notebook computer, or the like. For example, processor 203, storage 213, user interface display 204, and camera 206 may be elements of a tablet computer (or other portable computing device) that is mounted on a kiosk 201. Similarly, user interface 102, touch screen 107, and camera 105 on kiosk 100 (FIG. 1) may also be elements of a tablet computer or portable computing device.

Prescription confirmation system 202 may be connected to or in communication with one or more kiosks, such as a plurality of self-service kiosks 201 deployed in different retail locations. Prescription confirmation System 202 may provide support for verifying prescription data with a prescribing doctor or service authorized by the doctor and/or patient for prescription verification. Prescription confirmation system 202 may be a server or other computer, for example, comprising processor 218, storage device 219, WiFi router 220, and/or network interface 221.

Processor 218 controls and coordinates the operation of system 202 and its components using one or more software applications 222-223. Storage device 219 may be used to store software code and instructions for applications 222-223 and other data, such as customer and prescription information. Storage device 219 may be any appropriate memory device or computer storage media, such as, but not limited to, a hard disk drive, RAM, ROM, EEPROM, flash memory or other memory technology, CD-ROM, digital versatile disks (DVD) or other optical disk storage, magnetic cassettes, magnetic tape, magnetic disk storage or other magnetic storage devices. Prescription confirmation system 202 may communicate with kiosk 201 via a wireless or wired network connection. WiFi router 220 or another wireless transceiver supports wireless communications with kiosk 201 either directly or through one or more intermediate access points or networks (not shown) using RF signals transmitted and received using antenna 226. In other embodiments, prescription confirmation system 202 communicates with kiosk 201 via a public or private network(s) 216, which is accessed via a network interface 221.

Prescription confirmation application 222 provides support for prescription verification, to ensure validity and accuracy of prescriptions. Prescription confirmation system 202 and/or kiosk 201 may communicate with a prescribing doctor via a web service that is configured to verify prescriptions or any other service authorized by the doctor to perform verification via network 216, for example.

Kiosk interface application 223 provides communication between system 202 and a plurality of kiosks 201 to support, for example, receiving customer prescription information, monitoring the status of kiosk 201, providing software updates and other data to kiosk 201, and/or any other information.

Operating system 224 manages resources for processor 218 and provides services for applications 222 and 223 and other programs Applications 222 and 223 may be components of operating system 224 or may be separate software programs running on processor 218.

In various embodiments, a customer can also order eyewear using a remote terminal 230, which may be, for example, a desktop or personal computer, laptop computer, tablet computer, smartphone, mobile computing device, personal digital assistance (PDA), or other processor-based device that is capable of communication with kiosk 201. The customer may initiate and save a new order from terminal 230, or may complete or revise an existing order on kiosk 201, which was started from terminal 230. For example, the customer may start an order using any type of remote terminal, such as a laptop, notebook, tablet, mobile phone, PDA, desktop computer, or the same or a different kiosk, and then finish the order at kiosk 201.

FIG. 3 is a block diagram of various components of an embodiment of an automated eyewear kiosk 300. The kiosk 300 includes a customer interface 301, an information technology unit 302, a variable injection molding unit 303, a robotic arm 304, a micro coating unit 305, a frame injection molding unit 306, a packing unit 307, and a holding and dispensing unit 308. In various embodiments, kiosk 300 may also include an auto refracting unit (not shown) for generating customer prescription information. Additionally, not all of the described components 301-308 need to be present in every case. Some embodiments may contain additional components, such as a digital surfacing unit, a multi-dimensional printing unit (such as a 3-D printer) for manufacturing frames and/or lenses, or a number of other manufacturing components.

The customer interface 301 may be configured for displaying product information as well as accepting customer prescription information, frame data (including style, temple length, color, etc.), lens selection, and other order related information. After completing his or her order entry, the customer provides payment using the customer interface 301. The customer interface is additionally described in greater detail in FIG. 2.

An information technology unit 302 receives prescription data and performs calculations for the input needed by the variable injection molding unit 303, as well as information needed by any other component in the kiosk 300. The variable injection molding unit 303 uses injection molding to mold lenses corresponding to the entered prescription and in the exact shape needed to fit the selected frame. In addition to molding lenses corresponding to a specific prescription, in various embodiments, certain coatings or added value coatings such as photochromic coatings or electrochromic coatings, polarizing coatings or blue light blocking coatings, antistatic coatings, etc., or even electronics for various purposes, may be incorporated into the lens at this time.

In one or more embodiments, the injection molding unit 303 incorporates one or more specially shaped tab as part of the lens. The tab is shaped to facilitate placement of the lens within the selected frame in an easier and more secure way than traditionally used for eyeglasses. The tab may be formed during the injection molding process by the injection molding unit 303, but may also be formed after molding occurs using other methods not described. Also, the tab may protrude from a lens, or for some lens, the tab may be formed by carving out part of the lens material, or any other number of ways.

In various embodiments, lenses may be retained in the frames using elastic cushion connectors. At least one tab may be disposed or defined at an edge of a lens, extending from the lens. These tabs may be attached to the lens, formed or shaped from the lens, or the like, so as to extend from the lens. Corresponding fittings are defined by an eyeglasses frame, with each fitting positioned to correspond to a tab extending from the lens. The eyeglass frame may be formed in the frame injection molding unit 306, described below in greater detail. Each fitting may be defined by an interior socket larger than its corresponding tab. An elastic cushion connector may also be disposed between each of the fittings and the corresponding tab, in the fitting socket and at least partially around the corresponding tab, flexibly securing the lens into the frame.

In other embodiments, rather than, or in addition to injection molding unit 303, a digital surfacing unit (not shown) may be used for manufacturing lenses within the kiosk 300.

The lens formed in the injection molding unit 303, or otherwise, is moved by robotic arm 304 to micro coating unit 305. In addition to the robotic arm 304, other types of automated conveyance may be used, as well. The micro coating unit 305 provides hard multi coating (HMC) or other added value coatings, which may have been selected by the customer, or is otherwise standard for the lens. Examples of added value coatings include smudge and scratch protection, glare protection, etc. Once coatings have been applied in the micro coating unit 305, the lenses are then transferred by the robotic arm 304 to the packing unit 307 for packaging. In various embodiments, coatings may be applied as a film, by using lens inserts, spun or dipped directly on the lens, by coating transfer or film lamination technology, or any number of ways commonly known in the art.

In various embodiments, the frames selected by the customer are also manufactured within the kiosk 300. The specified frame and temples may be created in the shape and color selected by the customer using frame injection molding unit 306. Frame injection molding unit 306 may additionally incorporate tab cushions or sockets within the design that would couple together with the tabs generated on the lens by the injection molding unit 303, described previously. As with the lens tabs, the tab cushions or sockets facilitate an easier and more secure coupling of the lens to the frame. In various embodiments, the frames may be of any frame type, such as full frame, semi-rimless, or rimless. After completion of the frame in the frame injection molding unit 306, the frame is cooled and pieces are moved to packaging unit 307 by robotic arm 304.

Packing unit 307 seals the frame and lenses together along with generated instructions for assembly of the eyewear by the customer. In one embodiment the frame is molded to accept the lens with tabs and the frame temples are made to be inserted and locked into the frame. From the packing unit 307, robotic arm 304 places the packaged eyewear components into holding and dispensing unit 308. In various embodiments, eyeglasses may be packaged in a fully assembled, partially assembled, or completely disassembled state.

A customer is given notification that their eyewear is ready to be retrieved, upon delivery to the holding and dispensing unit 308. In one embodiment, the customer retrieves their order by entering an authorization code previously communicated by the kiosk 300 to the customer, in order to ensure the correct order is dispensed from the kiosk 300.

In other embodiments, rather than being manufactured within the kiosk 300 itself, the lens, the frames, or both may be manufactured remotely and then stocked within the kiosk for dispensing. For example, a kiosk 300 that only dispenses remotely manufactured eyewear components could be stocked with a few basic frame designs and the most commonly prescribed lenses, which have been remotely manufactured to fit the frames. Rather than retrieving injected frames from the frame injection molding unit 306 and the micro coating unit 305, the packing unit 307 would receive the remotely made frames and/or lenses from storage (not shown) within the kiosk 300 to package together for the customer.

FIG. 4 is a flowchart 400 illustrating a process for fulfilling customer orders for eyewear according to one embodiment. A customer visits or otherwise communicates with an automated eyewear kiosk, such as kiosk 100 or 201, for example. In step 401, order data is received at a kiosk. The order data may include prescription information, one or more frame styles in which a pair of lenses may be secured, coatings, additional lens types (such as polarized or tinted, that would also fit in the selected frame, or any other information necessary to complete an eyewear transaction. Although example embodiments described herein generally refer to prescription eyewear, it will be understood that the automated eyewear kiosk may be used to purchase any type of eyewear. For example, the customer may purchase prescription and non-prescription eyeglasses, reading glasses, sunglasses, protective eyewear, safety goggles, and athletic eyewear. In various embodiments, frame materials may be any type of material such as plastic, metal, wood, etc. and is not necessarily limited to material that can be injection molded.

After either manufacturing the lens and/or frames, or selecting from pre-manufactured lenses and/or frames, in step 402, the lenses may be dispensed from the kiosk, which corresponds to the prescription information provided in the order data. The lenses that are dispensed, in various embodiments, are manufactured with tabs for securing the lens, as described previously. In step 403, frames that have been manufactured with corresponding sockets for the lenses are dispensed. In various embodiments, step 402 and 403 occur simultaneously.

Many modifications and other embodiments of the invention will come to mind to one skilled in the art to which this invention pertains having the benefit of the teachings presented in the foregoing descriptions, and the associated drawings. Therefore, it is to be understood that the invention is not to be limited to the specific embodiments disclosed. Although specific terms are employed herein, they are used in a generic and descriptive sense only and not for purposes of limitation.

The invention claimed is:

1. An automated eyewear kiosk, comprising:
   a display configured to depict available frame and lens options to a customer;
   a user interface configured to receive eyewear order information, the eyewear order information comprising:
   customer prescription information and frame selection;

a lens manufacturing device being wholly contained within the automated eyewear kiosk and configured to manufacture lenses in a prescription of the customer and adapted for a selected frame; and a dispensing mechanism configured to dispense the manufactured lenses and the selected frame from the kiosk, wherein the lens manufacturing device uses injection molding to manufacture the lenses, and wherein the lenses are specifically adapted for the selected frame.

2. The automated eyewear kiosk of claim 1, wherein the selected frame is manufactured within the automated eyewear kiosk using multi-dimensional printing technology.

3. The automated eyewear kiosk of claim 1, wherein the lens manufacturing device uses digital surfacing to manufacture the lenses.

4. The automated eyewear kiosk of claim 1, wherein the selected frame is pre-manufactured and placed into the kiosk for dispensing with the lenses.

5. The automated eyewear kiosk of claim 1, further comprising a network interface configured to receive at least one of patient prescription information and a doctor verification of the prescription information.

6. A method for dispensing eyewear, comprising:
receiving order data at a kiosk, the order data comprising: optical lens prescription information, a frame selection, and patient identification data;
dispensing, from the kiosk, optical lenses corresponding to the received optical lens prescription information, wherein the optical lenses are manufactured by injection molding within the kiosk with tabs to secure and specifically adapt the optical lenses to the selected frame; and
dispensing, from the kiosk, the selected frame wherein the selected frame is manufactured with corresponding sockets to secure the optical lenses.

7. The method of claim 6, wherein receiving the order data further comprises receiving a request for more than one frame in which the optical lenses are secured.

8. The method of claim 6, wherein receiving order data further comprises receiving a request for more than one type of lens, each optical lens of the more than one type of lens being compatible with the selected frame.

9. The method of claim 6, further comprising using multi-dimensional printing technology to manufacture the selected frame within the kiosk.

10. The method of claim 6, further comprising utilizing digital surfacing to manufacture the optical lenses.

11. The method of claim 6, further comprising:
pre-manufacturing the selected frame; and
placing the selected frame into the kiosk for dispensing with the optical lenses.

12. The method of claim 6, further comprising utilizing a network interface configured to receive at least one of patient prescription information and a doctor verification of the prescription information.

13. An automated eyewear kiosk, comprising:
a display configured to depict available frame and lens options to a customer;
a user interface configured to receive eyewear order information, the eyewear order information comprising customer prescription information and frame selection;
a lens manufacturing device being wholly contained within the automated eyewear kiosk and configured to manufacture lenses in a prescription of the customer and adapted for a selected frame; and
a dispensing mechanism configured to dispense manufactured lenses and the selected frame from the kiosk, wherein the lens manufacturing device uses multi-dimensional printing to manufacture at least one of the frames and lenses, and wherein the lenses are specifically adapted for the selected frame.

\* \* \* \* \*